United States Patent
Jin et al.

(10) Patent No.: US 9,591,970 B2
(45) Date of Patent: Mar. 14, 2017

(54) METHOD, APPARATUS, AND SYSTEM FOR GENERATING DIAGNOSTIC IMAGE USING PHOTOACOUSTIC MATERIAL

(71) Applicant: SAMSUNG MEDISON CO., LTD., Hongcheon-gun, Gangwon-do (KR)

(72) Inventors: Gil-Ju Jin, Gangwon-do (KR); Dal-Kwon Koh, Gangwon-do (KR); Mi-Jeoung Ahn, Gangwon-do (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 252 days.

(21) Appl. No.: 14/490,426

(22) Filed: Sep. 18, 2014

(65) Prior Publication Data

US 2015/0216419 A1    Aug. 6, 2015

(30) Foreign Application Priority Data

Feb. 3, 2014  (KR) ........................ 10-2014-0012211

(51) Int. Cl.
*A61B 8/08*        (2006.01)
*A61B 5/00*        (2006.01)
*A61B 8/00*        (2006.01)

(52) U.S. Cl.
CPC .......... *A61B 5/0095* (2013.01); *A61B 5/0035* (2013.01); *A61B 5/0071* (2013.01);
(Continued)

(58) Field of Classification Search
CPC ... A61B 5/0095; A61B 8/4477; A61B 8/5292; A61B 8/4281
See application file for complete search history.

(56) References Cited

U.S. PATENT DOCUMENTS

2003/0225320 A1   12/2003  Jeon et al.
2004/0131299 A1    7/2004  Adoram et al.
(Continued)

FOREIGN PATENT DOCUMENTS

JP      2012-231878 A    11/2012
WO      2009/057021 A2    5/2009
(Continued)

OTHER PUBLICATIONS

International Search Report issued in International Application No. PCT/KR2014/006921 dated Nov. 26, 2014.
(Continued)

*Primary Examiner* — Joel Lamprecht
(74) *Attorney, Agent, or Firm* — McDermott Will & Emery LLP (57) ABSTRACT

Disclosed is a method of generating a diagnostic image by using a photoacoustic material. The method includes determining a wavelength band of light maximally absorbed by a photoacoustic material, based on at least one or more photoacoustic materials injected into an object, irradiating light, which corresponds to the determined wavelength band, onto an internal region of interest (ROI) of the object to acquire a photoacoustic signal corresponding to the irradiated light, generating a photoacoustic image indicating the ROI by using the photoacoustic signal, and combining and displaying the generated photoacoustic image and an image expressing that the light is being irradiated onto the ROI.

20 Claims, 8 Drawing Sheets

(52) U.S. Cl.
CPC ............ *A61B 5/415* (2013.01); *A61B 5/7425* (2013.01); *A61B 8/4416* (2013.01); *A61B 8/481* (2013.01); *A61B 8/5261* (2013.01)

(56) References Cited

U.S. PATENT DOCUMENTS

| | | |
|---|---|---|
| 2009/0105588 A1 | 4/2009 | Emelianov et al. |
| 2011/0021924 A1* | 1/2011 | Sethuraman ......... A61B 5/0095 600/463 |
| 2012/0065494 A1* | 3/2012 | Gertner ................. A61B 5/055 600/411 |
| 2013/0006088 A1 | 1/2013 | Miyasato |
| 2013/0160558 A1 | 6/2013 | Oishi |
| 2013/0218024 A1 | 8/2013 | Boctor et al. |
| 2013/0336551 A1* | 12/2013 | Clingman ............ A61B 5/0095 382/128 |
| 2014/0024918 A1 | 1/2014 | Hirota |

FOREIGN PATENT DOCUMENTS

| | | |
|---|---|---|
| WO | 2012/085751 A1 | 6/2012 |
| WO | 2013/188707 A1 | 12/2013 |

OTHER PUBLICATIONS

Notice of Non-Final Rejection dated Jun. 1, 2015 issued in Korean Patent Application No. 10-2014-0012211 (English translation).
Korean Notice of Allowance issued in Application No. 10-2014-0012211 dated Jun. 21, 2016, with English translation.

* cited by examiner

METHOD, APPARATUS, AND SYSTEM FOR GENERATING DIAGNOSTIC IMAGE USING PHOTOACOUSTIC MATERIAL

RELATED APPLICATIONS

This application claims the benefit of Korean Patent Application No. 10-2014-0012211, filed on Feb. 3, 2014, in the Korean Intellectual Property Office, the disclosure of which is incorporated herein in its entirety by reference.

BACKGROUND

1. Field

One or more embodiments of the present invention relate to a method, apparatus, and system for generating a diagnostic image using a photoacoustic material.

2. Description of the Related Art

Photoacoustic imaging technology provides an image of deep tissue, having a clear contrast effect obtained by optical absorption and a high resolution obtained by an ultrasound wave. The principle of the photoacoustic imaging technology is as follows. Local heat accumulation based on irradiation of a momentary laser pulse generates an acoustic wave, which is propagated and detected by an ultrasound imaging scanner.

The photoacoustic imaging technology has been already studied at a considerable level by targeting a brain, heart, eyeball, or cancer cells of a small animal. Furthermore, with a natural mergence trend of excitation light detection and ultrasound wave detection, a photoacoustic imaging system may be easily integrated with the existing ultrasound imaging system through only a simple alternation (for example, an ultrasound wave transmitting function is removed, and a radio frequency (RF) data collecting function is added). Such an integration system shares an acoustic detector with other systems, and thus provides portability and a real-time imaging ability of a conventional ultrasound imaging system.

In addition, much research has been conducted into a contrast medium for expressing an imaging modality in two methods, for enhancing detection sensitivity and singularity. For example, a light-absorbing organic dye, a plasmonic gold nanostructure, and organic nanoparticles have been developed for photoacoustic imaging in various biological application fields.

At present, a dye (for example, methylene blue, idocyanine green, etc.) whose use is clinically allowed may be considered as a promising candidate of a photoacoustic contrast medium which is clinically available. Methylene blue has been shown to be usable as a photoacoustic lymphatic gland tracer for diagnosing breast cancer.

SUMMARY

One or more embodiments of the present invention include a method, apparatus, and system for generating a diagnostic image using a photoacoustic material.

One or more embodiments of the present invention include a non-transitory computer-readable storage medium storing a program for executing the method in a computer.

Additional aspects will be set forth in part in the description which follows and, in part, will be apparent from the description, or may be learned by practice of the presented embodiments.

According to one or more embodiments of the present invention, a method of generating a diagnostic image includes: determining a wavelength band of light maximally absorbed by a photoacoustic material, based on at least one or more the photoacoustic materials injected into an object; irradiating light that corresponds to the determined wavelength band onto an internal region of interest (ROI) of the object and acquiring a photoacoustic signal corresponding to the irradiated light; generating a photoacoustic image indicating the ROI by using the photoacoustic signal; and combining the generated photoacoustic image and an image expressing that the light is being irradiated onto the ROI and displaying the combined image.

According to one or more embodiments of the present invention, provided is a non-transitory computer-readable storage medium storing a program for executing the diagnostic image generating method.

According to one or more embodiments of the present invention, an apparatus for generating a diagnostic image includes: a determiner configured to determine a wavelength band of light maximally absorbed by a photoacoustic material, based on at least one or more photoacoustic materials injected into an object; a light generator configured to generate light corresponding to the determined wavelength band; an image generator configured to generate a photoacoustic image indicating an internal region of interest (ROI) of the object and an image expressing that the light is being irradiated onto the ROI, by using the photoacoustic signal; and a display unit configured to combine the photoacoustic image and the image expressing that the light is being irradiated onto the ROI and display the combined image.

According to one or more embodiments of the present invention, a system includes: a probe that irradiates light onto an internal region of interest (ROI) of an object to acquire a photoacoustic signal corresponding to the irradiated light; and a diagnostic image generating apparatus that generates light which is to be irradiated onto the ROI, based on at least one or more photoacoustic materials injected into the object, generates a photoacoustic image indicating the ROI and an image expressing that the light is being irradiated onto the ROI, by using the photoacoustic signal, and combines and displays the generated images.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Also, numerous modifications and adaptations will be readily apparent to those of ordinary skill in the art without departing from the spirit and scope of the present invention.

Figure 1:
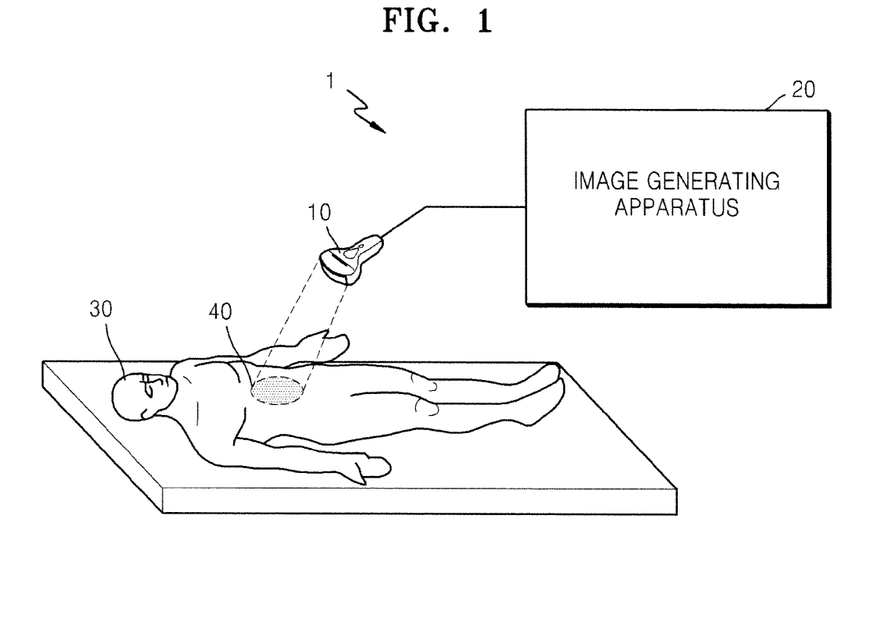
FIG. 1 is a diagram illustrating an example of a diagnostic image generating system according to an embodiment.

FIG. 1 is a diagram illustrating an example of a diagnostic image generating system 1 according to an embodiment.

Referring to FIG. 1, the diagnostic image generating system 1 includes a probe 10 and an image generating apparatus 20.

The probe 10 irradiates light onto a region of interest (ROI) 40 of an object 30, and acquires a photoacoustic signal corresponding to the irradiated light. Here, the object 30 denotes a target object from which a diagnostic image is to be generated, and for example, may be a patient. However, the object 30 is not limited thereto. According to an embodiment of the present invention, a photoacoustic material is injected into the object 30 before the light is irradiated. The photoacoustic material causes a photoacoustic effect due to the light irradiated onto the ROI 40.

Hereinafter, the photoacoustic material is described as denoting a colored microbubble, but is not limited thereto. In other words, each of materials that show the photoacoustic effect based on the irradiated light may correspond to the photoacoustic material without limitation. The colored microbubble to be described below as the photoacoustic material is a dual modality contrast medium, and may be effectively used for ultrasound and photoacoustic imaging.

The colored microbubble includes a dye-colored lipid shell and a charging gas that fills an inside of the lipid shell. Here, the dye absorbs the light irradiated from the probe 10. The dye absorbing the light causes a heat deposit of the dye and the lipid shell. Due to the heat deposit, the dye or the lipid shell generates an acoustic wave. For example, the dye may absorb incident light having a wavelength within a range of about 500 nm to about 1,300 nm, but is not limited thereto.

A photoacoustic signal, generated from the dye, the dye-colored lipid shell, or a slice of the dye-colored lipid shell, may be, for example, a signal having a frequency of about 1 MHz to about 50 MHz. Here, the photoacoustic signal is detected by an ultrasound signal transceiver 120 included in the probe 10.

For example, the dye may be azure blue, Evans blue, idocyanine green, brilliant blue, Nile blue, methylene blue, or a combination thereof. The above-described examples of the dye may be non-toxic and biodegradable.

The dye-colored shell acts as a vessel that contains a charging gas and/or a charging material, such as a drug, in an internal space thereof. A microbubble, having a shell filled with the charging gas, may transmit an ultrasound wave. A microbubble having a drug-containing shell may act as a drug porter.

The shape of the shell is not limited, but the shell is generally spherical in shape. For example, a particle size of the shell may be about 0.5 μm to about 10 μm.

The ROI 40 denotes a certain region of the object 30 from which the diagnostic image is generated, and for example, may correspond to a region including a lesion tissue. However, the ROI 40 is not limited thereto.

The probe 10 irradiates the light onto the ROI 40, and due to the light, thermal expansion occurs in the photoacoustic material injected into the object 30. The photoacoustic signal is generated by the thermal expansion, and the probe 10 receives the photoacoustic signal. The probe 10 irradiates the light onto the ROI 40, and details for receiving the photoacoustic signal will be described below with reference to FIG. 2.

Figure 2:
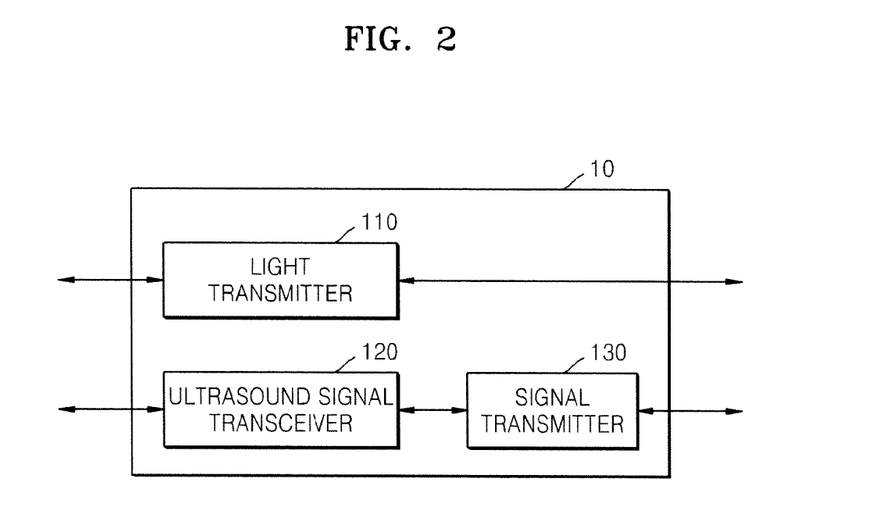
FIG. 2 is a block diagram illustrating an example of a probe according to an embodiment.

FIG. 2 is a block diagram illustrating an example of the probe 10 according to an embodiment.

Referring to FIG. 2, the probe 10 includes a light receiver 110, the ultrasound signal transceiver 120, and a signal transmitter 130. The probe 10 of FIG. 2 is illustrated as including only elements associated with the present embodiment. Therefore, it may be understood by those of ordinary skill in the art that the probe 10 may further include general-use elements in addition to the elements of FIG. 2. Also, each of the light receiver 110, ultrasound signal transceiver 120, and signal transmitter 130 of the probe 10 of FIG. 2 may be provided as a separate apparatus.

The probe 10 according to an embodiment of the present invention irradiates the light onto the ROI 40, and acquires the photoacoustic signal corresponding to the irradiated light. In addition, when it is assumed that a photoacoustic material is in the form of the above-described microbubble, the probe 10 may transmit an ultrasound signal (hereinafter referred to as a first ultrasound signal), which is used to break the microbubble, to the ROI 40. Also, the probe 10 may transmit another ultrasound signal (hereinafter referred to as a second ultrasound signal), which is used to generate an ultrasound image, to the ROI 40, and acquire an echo signal corresponding to the second ultrasound signal.

In other words, the probe 10 may irradiate light which is used to generate a photoacoustic image indicating the ROI 40 with the photoacoustic material provided therein, or irradiate an ultrasound signal which is used to generate an ultrasound image indicating the ROI 40. Here, the ultrasound image includes a brightness (B) mode image, a motion (M) mode image, a Doppler mode image, a color (C) mode image, and an elastic mode image.

Hereinafter, operations of the light receiver 110, the ultrasound signal transceiver 120, and the signal transmitter 130 which are included in the probe 10 will be described in detail.

The ultrasound signal transceiver 120 may irradiate the second ultrasound signal having a low mechanical index (MI) onto the ROI 40. The irradiated second ultrasound signal is reflected from an internal microbubble of the ROI 40, thereby generating an echo signal.

Here, the second ultrasound signal has the low MI. The MI denotes a numerical value which is determined by using a lowest pressure and central frequency of an ultrasound wave. The MI is a numerical value indicating a degree of a bio-effect obtained by an ultrasound wave, and as the MI becomes higher, an effect of the MI on a human body increases. For example, the second ultrasound signal may have a low MI having a range of about 0.2 to less than about 0.5. Due to the low MI, the microbubble used as the photoacoustic material is not broken. Therefore, the microbubble in the ROI 40 onto which the second ultrasound signal is irradiated may generate an echo signal without being broken.

Moreover, the ultrasound signal transceiver 120 may irradiate the first ultrasound signal having a high MI onto the ROI 40. The irradiated first ultrasound signal breaks the microbubble in the ROI 40. When the mircrobubble is broken, an internal charging material (for example, a charging gas or a drug) of the microbubble is emitted and supplied to the ROI 40, and moreover, slices of the microbubble (i.e., broken microbubbles) are produced.

The first ultrasound signal may have a high MI. For example, the first ultrasound signal may have the high MI having a range of about 0.5 to about 1.9. Due to the high MI, the microbubble used as the photoacoustic material may be broken. Therefore, the microbubble is broken to emit an internal charging material thereof, and simultaneously, slices of the microbubble are produced.

The light transmitter 110 irradiates the light onto the ROI 40. The light irradiated by the light transmitter 110 may correspond to all kinds of optical stimulus signals. The below-described light generator 220 included in the image generating apparatus 20 may set an intensity and wavelength band of light irradiated from the light transmitter 110. When the light transmitter 110 irradiates light having certain intensity or more onto the ROI 40, microbubble slices in the ROI 40 absorb the light. Thermal expansion occurs in the microbubble slices that have absorbed energy, and a photoacoustic signal is generated due to the thermal expansion. This is called a photoacoustic effect.

The light transmitter 110 may be physically separated from the probe 10, or may be provided outside the probe 10.

The ultrasound signal transceiver 120 acquires a photoacoustic signal and an echo signal. The signal transmitter 130 transmits the photoacoustic signal and the echo signal, acquired by the ultrasound signal transceiver 120, to the image generating apparatus 20.

Figure 3:
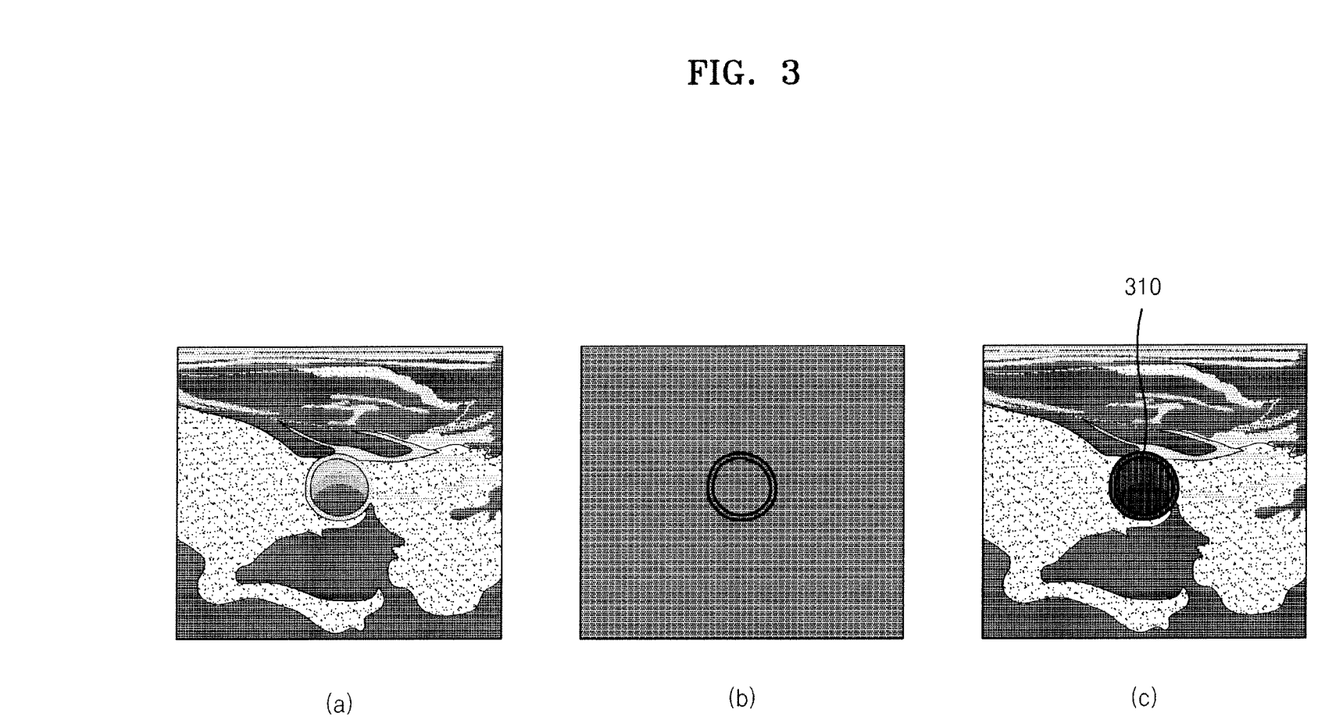
FIG. 3 illustrates diagrams for describing an example of an image generated by using a photoacoustic signal and an echo signal which are acquired by a probe according to an embodiment.

FIG. 3 illustrates diagrams for describing an example of an image generated by using a photoacoustic signal and an echo signal which are acquired by the probe according to an embodiment.

Referring to FIG. 3(*a*), an example of an ultrasound image which the image generating apparatus 20 generates by using the echo signal received from the probe 10 is illustrated. In FIG. 3(*a*), the ultrasound image is illustrated as a B mode image, but is not limited thereto. For example, the ultrasound image may be an M mode image, a Doppler mode image, a C mode image, or an elastic mode image.

Referring to FIG. 3(*b*), an example of a photoacoustic image which the image generating apparatus 20 generates by using the photoacoustic signal received from the probe 10 is illustrated.

Referring to FIG. 3(*c*), an example of an image which is generated by synthesizing an ultrasound image and a photoacoustic image in the image generating apparatus 20 is illustrated. The image generator 230 included in the image generating apparatus 20 may separately generate the ultrasound image and the photoacoustic image, and may generate an image which is obtained by synthesizing the two images. Therefore, by using the synthesized image, a user knows a photoacoustic material being located at an internal position 310 of an ROI.

Referring again to FIG. 1, the image generating apparatus 20 generates light which is to be irradiated onto an ROI, based on a photoacoustic material. Also, the image generating apparatus 20 generates a photoacoustic image indicating the ROI and an image indicating that the light is being irradiated onto the ROI, by using a photoacoustic signal. Also, the image generating apparatus 20 combines and displays the generated images. A detailed operation of the image generating apparatus 20 will be described below with reference to FIGS. 4 to 10.

Figure 4:
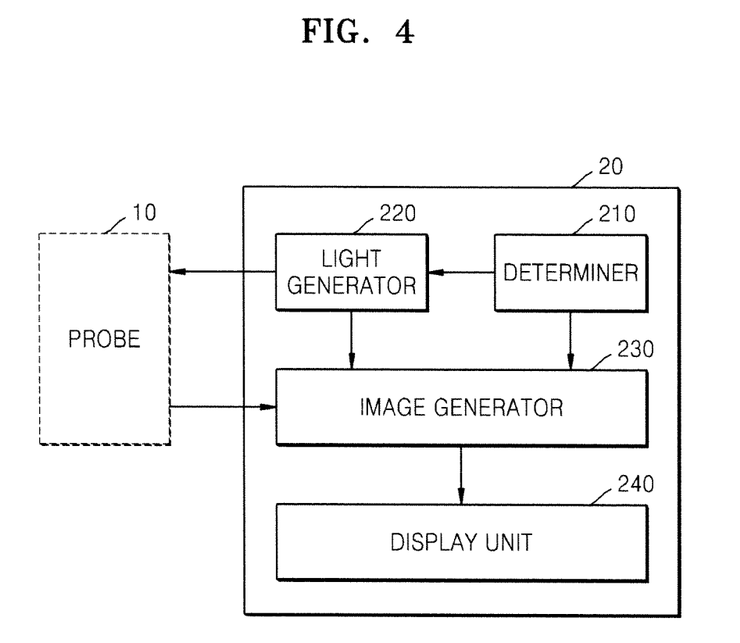
FIG. 4 is a block diagram illustrating an example of an image generating apparatus according to an embodiment.

FIG. 4 is a block diagram illustrating an example of the image generating apparatus 20 according to an embodiment.

Referring to FIG. 4, the image generating apparatus 20 includes a determiner 210, a light generator 220, an image generator 230, and a display unit 240. The image generating apparatus 20 of FIG. 4 is illustrated as including only elements associated with the present embodiment. Therefore, it may be understood by those of ordinary skill in the art that the image generating apparatus 20 may further include general-use elements in addition to the elements of FIG. 4.

The determiner 210, light generator 220, and image generator 230 of the image generating apparatus 20 of FIG. 4 may correspond to one or more processors. Each of the processors may be implemented as an array of a plurality of logic gates, or may be implemented as a combination of a general-use microprocessor and a memory that stores a program executable by the microprocessor. Also, it may be understood by those of ordinary skill in the art that the elements may be implemented as another type of hardware.

The determiner 210 determines a wavelength band of light which is maximally absorbed by the photoacoustic material, based on at least one or more photoacoustic materials injected into an object. Here, the wavelength band may denote a portion of the wavelength band corresponding to visible light, or denote a portion of the wavelength band corresponding to light except for the visible light. Generally, the wavelength band corresponding to the visible light denotes a wavelength band of about 400 nm to about 800 nm, and a certain color is shown in light having the wavelength band corresponding to the visible light. On the other hand, no color is shown in light having the wavelength band corresponding to the light except for the visible light.

For example, based on the photoacoustic material, the determiner 210 may determine a portion of the wavelength band, corresponding to the visible light, as a wavelength band of light. An example in which the determiner 210 determines a wavelength band of light will be described with reference to FIG. 5.

Figure 5:
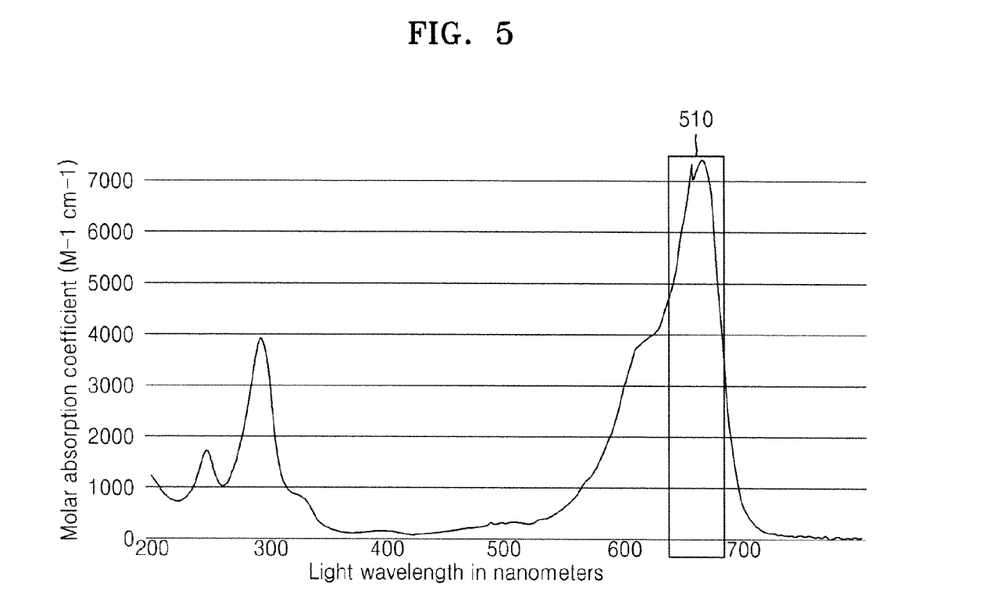
FIG. 5 is a diagram for describing an example in which a determiner according to an embodiment determines a wavelength band of light.

FIG. 5 is a diagram for describing an example in which a determiner according to an embodiment determines a wavelength band of light.

Referring to FIG. 5, a graph that shows a light absorption rate of methylene blue based on a wavelength band of light is shown. In detail, in comparison to light having another wavelength band, methylene blue absorbs more light having a wavelength band 510 of about 650 nm. Therefore, when the light irradiated from the probe 10 has the wavelength band 510 of about 650 nm, a high-quality photoacoustic image may be generated.

For example, when it is assumed that a photoacoustic material (in detail, a dye contained in a microbubble) injected into the object 30 is methylene blue, the determiner 210 determines the wavelength band 510 of about 650 nm, which is a wavelength band of light maximally absorbed by methylene blue, as a wavelength band of the light which is to be irradiated from the probe 10.

A storage unit (not shown) included in the image generating apparatus 20 may store information about dyes, which are usable as photoacoustic materials, and information about a wavelength band of light maximally absorbed by each of the dyes. Therefore, the determiner 210 may determine a wavelength band of light maximally absorbed by the photoacoustic material injected into the object 30, by using the information stored in the storage unit (not shown).

Referring again to FIG. 4, as another example, the determiner 210 may determine a portion of a wavelength band, corresponding to light except visible light, as a wavelength band of light on the basis of a photoacoustic material. In other words, by using the information stored in the storage unit (not shown), the determiner 210 may determine a wavelength band of light, which is maximally absorbed by the photoacoustic material, as a portion of the wavelength band corresponding to the light except the visible light. In this case, the below-described image generator 230 displays a region, corresponding to a position of the photoacoustic material in a photoacoustic image, in a certain color, and displays, in a certain color, the shape of light in an image indicating that the light is being irradiated onto an ROI.

The light generator 220 generates light corresponding to the determined wavelength band. In other words, the light generator 220 generates a light signal having the wavelength band determined by the determiner 210. Furthermore, the light generator 220 transmits the generated light signal to the light transmitter 110 of the probe 10.

The image generator 230 generates a photoacoustic image (hereinafter referred to as a first image) indicating the ROI 40 by using a photoacoustic signal corresponding to the light. Also, the image generator 230 generates an image (hereinafter referred to as a second image) indicating that the light is being irradiated onto the ROI 40.

In detail, when generating the first image, the image generator 230 displays a region, corresponding to a position of a photoacoustic material in the first image, in a color corresponding to the wavelength band determined by the determiner 210. Also, when generating the second image, the image generator 230 displays the shape of light in the color, corresponding to the wavelength band determined by the determiner 210, in the second image. Hereinafter, an example in which the image generator 230 operates will be described with reference to FIG. 6.

Figure 6:
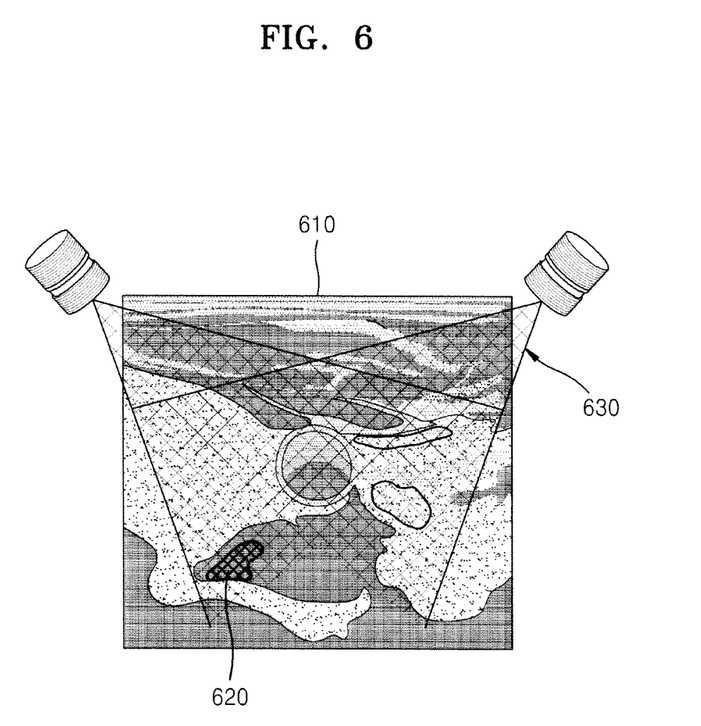
FIG. 6 is a diagram for describing an example in which an image generator according to an embodiment operates.

FIG. 6 is a diagram for describing an example in which the image generator according to an embodiment operates.

In FIG. 6, an image in which a first image, a second image, and an ultrasound image (which indicate an ROI 610) are combined is illustrated. In FIG. 6, for convenience of description, the combination image is merely illustrated, and the image generator 230 may separately generate the first image, the second image, and the ultrasound image.

The image generator 230 generates the first image by using the photoacoustic signal transmitted from the probe 10. In this case, the image generator 230 displays a region 620, corresponding to a position of a photoacoustic material in the first image, in a color corresponding to a wavelength band determined by the determiner 210. For example, when it is assumed that a dye contained in the photoacoustic material is methylene blue, a color corresponding to a wavelength band of about 650 nm, which is the wavelength band determined by the determiner 210, denotes blue. Therefore, the image generator 230 displays a region 620, corresponding to the position of the photoacoustic material in the first image, in blue.

Moreover, the image generator 230 generates the second image. For example, the image generator 230 may generate a shape 630, indicating that light is being spread toward the ROI 610, as the second image, but is not limited thereto. In other words, when indicating that the light is being irradiated onto the ROI 610, the second image is not limited to an image expressing a shape 630 in which the light is triangularly spread. In this case, the image generator 230 displays the shape 630 of the light in a color, corresponding to a wavelength band determined by the determiner 210, in the second image. For example, when it is assumed that the dye contained in the photoacoustic material is methylene blue, the image generator 230 displays the shape 630 of the light in blue, in the second image.

Referring again to FIG. 5, a wavelength band determined by the determiner 210 may be a portion of a wavelength band corresponding to light except visible light. In this case, the image generator 230 displays the region, corresponding to the position of the photoacoustic material in the first image, in a certain color (for example, green). Also, the image generator 230 displays the shape of the light in a certain color (for example, green), in the second image.

According the above description, the image generator 230 displays, in the same color, the region corresponding to the position of the photoacoustic material in the first image and the shape of the light in the second image. Therefore, through only a displayed image, a user easily recognizes the kind of a photoacoustic material and a wavelength band of the light irradiated from the probe 10.

Referring again to FIG. 5, examples of the photoacoustic material injected into the object 30 may include a plurality of different photoacoustic materials. In other words, the plurality of different photoacoustic materials may be injected into the object 30. In this case, the determiner 210 determines wavelength bands of light maximally absorbed by the photoacoustic materials injected into the object 30. The light generator 220 generates light signals respectively corresponding to the determined wavelength bands. The probe 10 sequentially irradiates the light by using the light signals transmitted from the light generator 220.

For example, when it is assumed that the photoacoustic materials injected into the object 30 are a, b, and c, the determiner 210 determines three wavelength bands respectively corresponding to the photoacoustic materials a, b, and c, and the light generator 220 generates three kinds of light signals respectively corresponding to the three wavelength bands. The probe 10 sequentially irradiates three kinds of light corresponding to the three kinds of light signals on the ROI 40, thereby acquiring a photoacoustic signal.

Therefore, the image generator 230 may generate first and second images corresponding to each of the photoacoustic materials a, b, and c injected into the object 30. In this case, as described above with reference to FIG. 6, the image generator 230 displays, in the same color, a region corresponding to a position of a photoacoustic material in the first image and the shape of light in the second image. An example, in which a plurality of the first images and second images generated from the photoacoustic materials are displayed, will be described below with reference to FIGS. 7 and 8.

The display unit 240 combines and displays a photoacoustic image and an image expressing that light is being irradiated. That is, the display unit 240 combines and displays the first and second images generated by the image generator 230. The display unit 240 may include an output device such as a display panel, a liquid crystal display (LCD) screen, or a monitor which is included in the image generating apparatus 20. In FIG. 4, the display unit 240 is illustrated as including the image generating apparatus 20, but may be provided as an image display device independent from the image generating apparatus 20.

For example, as illustrated in FIG. 6, the display unit 240 may combine and display the first image, the second image, and an ultrasound image of the ROI 40. Also, the display unit 240 may combine and display only the first and second images, or combine and display only the first image and the ultrasound image. Also, the display unit 240 may separately display the first image, the second image, and the ultrasound image.

Figure 7:
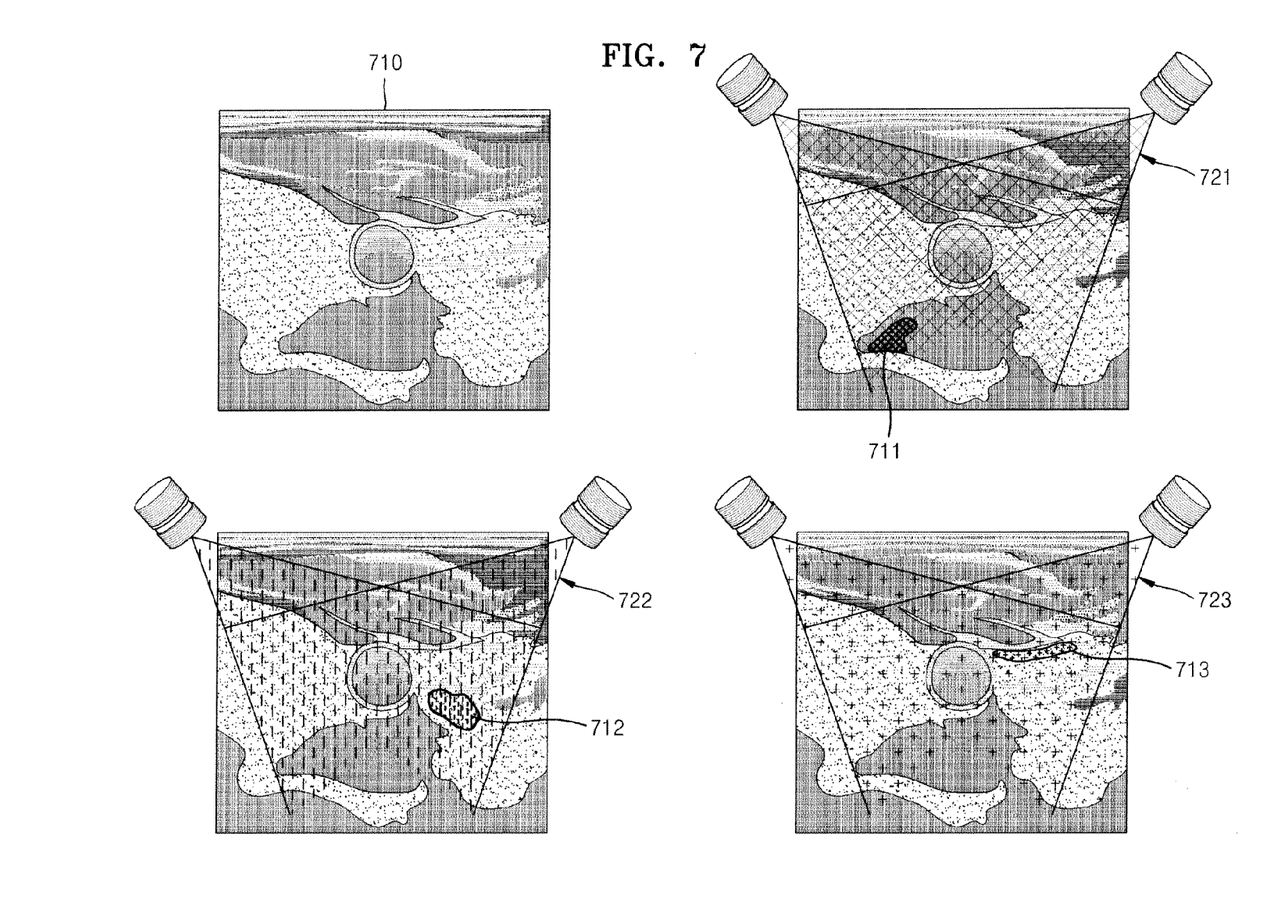
FIG. 7 is a diagram for describing an example in which a display unit according to an embodiment displays an image.
Figure 8:
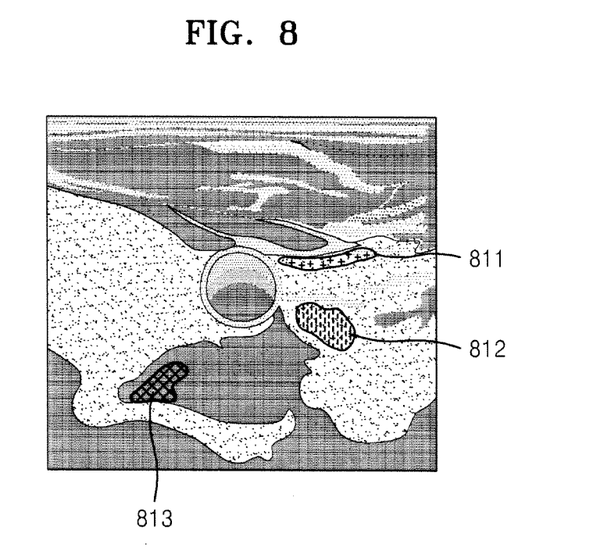
FIG. 8 is a diagram for describing another example in which the display unit according to an embodiment displays an image.

When a plurality of different photoacoustic materials are injected into the object 30, an example in which the display unit 240 displays an image will be described below with reference to FIGS. 7 to 8. In FIGS. 7 and 8, for convenience of description, it is assumed that three different kinds of photoacoustic materials a, b, and c are injected into the object 30.

FIG. 7 is a diagram for describing an example in which a display unit according to an embodiment displays an image.

Referring to FIG. 7, four different images displayed by the display unit 240 are illustrated. In detail, a left upper image denotes an ultrasound image indicating an ROI 710, and a right upper image denotes an image in which the ultrasound image, a first image corresponding to the photoacoustic material a, and a second image corresponding to the photoacoustic material a are combined. Also, a left lower image denotes an image in which the ultrasound image, a first image corresponding to the photoacoustic material b, and the second image corresponding to the photoacoustic material b are combined, and a right lower image denotes an image in which the ultrasound image, a first image corresponding to the photoacoustic material c, and a second image corresponding to the photoacoustic material c are combined.

That is, the display unit 240 may separate and display, by using a photoacoustic material, a photoacoustic image (i.e., a first image) and an image (i.e., a second image) expressing that light is being irradiated onto an ROI.

FIG. 8 is a diagram for describing another example in which the display unit according to an embodiment displays an image.

Referring to FIG. 8, one image displayed by the display unit 240 is illustrated. In detail, the image of FIG. 8 denotes an image in which an ultrasound image, a first image corresponding to the photoacoustic material a, a first image corresponding to the photoacoustic material b, and a first image corresponding to the photoacoustic material c are combined.

That is, the display unit 240 may display an image in which photoacoustic images (i.e., first images) respectively corresponding to a plurality of photoacoustic materials are combined.

Moreover, although not shown, the display unit 240 may display the image, in which the photoacoustic images (i.e., the first images) respectively corresponding to the plurality of photoacoustic materials are combined, and an image in which images (i.e., second images), expressing that light is being irradiated onto ROIs respectively corresponding to the photoacoustic materials, are combined. In this case, the display unit 240 may sequentially display the second images in correspondence with the order of light irradiated by the probe 10, thereby displaying the image in which the second images are combined.

According to the above description, even when a plurality of different photoacoustic materials are injected into the object 30, the display unit 240 may display the images, generated by the image generator 230, in combination or separately. Therefore, a user easily recognizes a region in which each of the photoacoustic materials is located.

Figure 9:
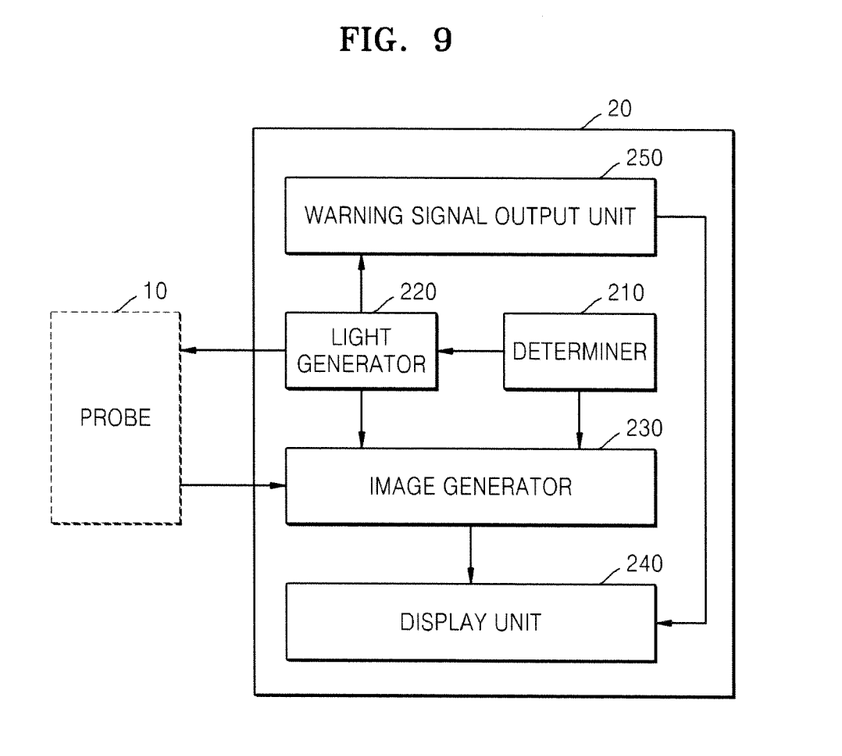
FIG. 9 is a block diagram illustrating another example of an image generating apparatus according to an embodiment.

FIG. 9 is a block diagram illustrating another example of an image generating apparatus 20 according to an embodiment.

Referring to FIG. 9, the image generating apparatus 20 includes a warning signal output unit 250 in addition to the determiner 210, the light generator 220, the image generator 230, and the display unit 240. The image generating apparatus 20 of FIG. 9 is illustrated as including only elements associated with the present embodiment. Therefore, it may be understood by those of ordinary skill in the art that the image generating apparatus 20 may further include general-use elements in addition to the elements of FIG. 4.

The determiner 210, the light generator 220, the image generator 230, and the warning signal output unit 250 of the image generating apparatus 20 of FIG. 9 may correspond to one or more processors. Each of the processors may be implemented as an array of a plurality of logic gates, or may be implemented as a combination of a general-use microprocessor and a memory that stores a program executable by the microprocessor. Also, it may be understood by those of ordinary skill in the art that the elements may be implemented as another type hardware.

Detailed descriptions of the determiner 210, the light generator 220, the image generator 230, and the display unit 240 of the image generating apparatus 20 of FIG. 9 are as described above with reference to FIG. 4, and thus are not repeated below.

The warning signal output unit 250 outputs a warning signal at a time when light is irradiated onto the ROI 40 of the object 30. Here, the warning signal may be one of a signal corresponding to a certain sound, a signal corresponding to a certain text, a signal corresponding to a certain vibration, and a signal corresponding to a certain image. In this case, when the warning signal is the signal corresponding to the certain text or the signal corresponding to the certain image, the warning signal output unit 250 may transmit the warning signal to the display unit 240, which may display the certain text or the certain image.

Figure 10:
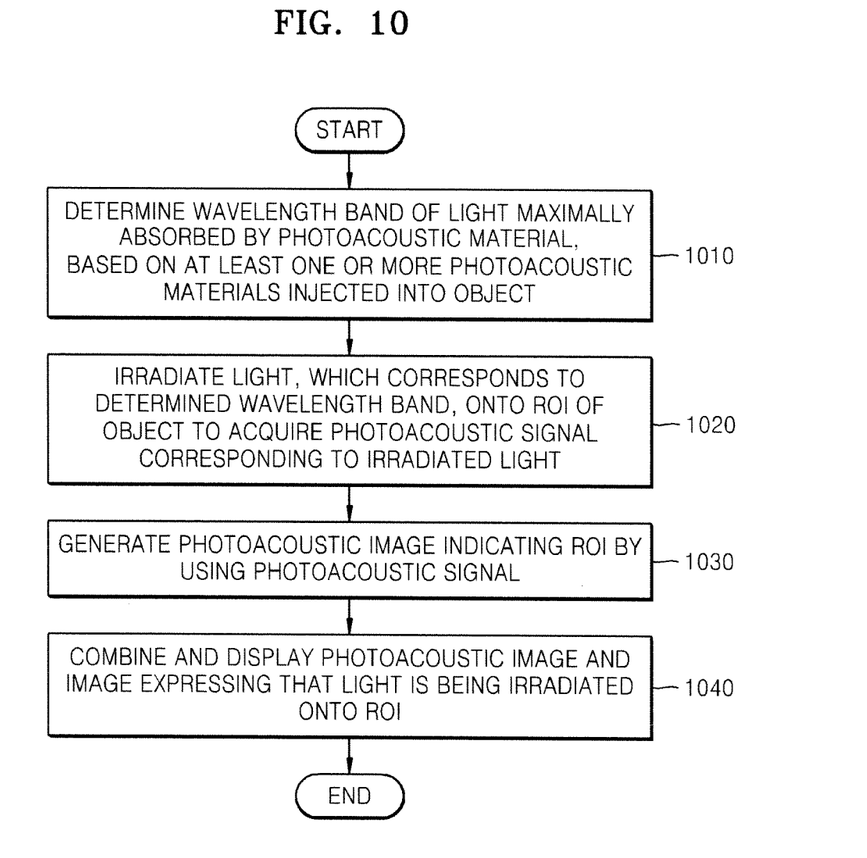
FIG. 10 is a flowchart illustrating an example of a diagnostic image generating method according to an embodiment.

FIG. 10 is a flowchart illustrating an example of a diagnostic image generating method according to an embodiment.

Referring to FIG. 10, the diagnostic image generating method includes a plurality of operations that are performed in time series by the system 1 or the image generating apparatus 20 of FIGS. 1, 4, and 9. Thus, although not described below, the above-described details of the system 1 or the image generating apparatus 20 of FIGS. 1, 4, and 9 may be applied to the diagnostic image generating method of FIG. 10.

In operation 1010, the image generating apparatus 20 determines a wavelength band of light maximally absorbed by a photoacoustic material, based on at least one or more photoacoustic materials injected into the object 30.

In operation 1020, the image generating apparatus 20 irradiates light, corresponding to the determined wavelength band, onto the ROI 40 of the object 30 to acquire a photoacoustic signal corresponding to the irradiated light.

In operation 1030, the image generating apparatus 20 generates a photoacoustic image indicating the ROI 40 by using the photoacoustic signal.

In operation 1040, the image generating apparatus 20 combines and displays the photoacoustic image and an image expressing that the light is being irradiated onto the ROI 40.

As described above, according to the one or more of the above embodiments of the present invention, a plurality of photoacoustic images are obtained based on a plurality of different photoacoustic materials, and are simultaneously displayed.

Moreover, even when photoacoustic materials having different colors are injected into an object together, the photoacoustic materials may be distinguished in a photoacoustic image.

The above-described method may be written as computer programs and may be implemented in general-use digital computers that execute the programs using computer-readable recording media. The information used in the aforementioned embodiments may be recorded in computer-readable recording media through various means. Program storage devices usable for describing a storage device including executable computer codes for performing various methods of the present invention should not be understood as including transitory targets like signals. Examples of the computer-readable recording medium include magnetic storage media (e.g., ROM, floppy disks, hard disks, etc.) and optical recording media (e.g., CD-ROMs or DVDs).

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of generating a diagnostic image, the method comprising:
   respectively determining a wavelength band of light maximally absorbed by a plurality of different photoacoustic materials, based on the plurality of different photoacoustic materials injected into an object;
   irradiating different lights, which correspond to the respectively determined wavelength bands, onto an internal region of interest (ROI) of the object and acquiring different photoacoustic signals corresponding to the irradiated light;
   generating different photoacoustic images indicating the ROI by using the different photoacoustic signals, wherein the different photoacoustic images correspond to the plurality of different photoacoustic materials respectively; and
   combining the generated different photoacoustic images and an image expressing that the lights are being irradiated onto the ROI and displaying the combined image.

2. The method of claim 1, wherein the determined wavelength band of the light comprises a portion of a wavelength band corresponding to visible light.

3. The method of claim 2, wherein the displaying comprises displaying a region, corresponding to a position of the photoacoustic material in the photoacoustic image, in a color corresponding to the determined wavelength band.

4. The method of claim 2, wherein the displaying comprises displaying a shape of the light in a color corresponding to the determined wavelength band, in the image expressing that the light is being irradiated onto the ROI.

5. The method of claim 1, wherein the determined wavelength, band of the light comprises a portion of a wavelength band corresponding to light except visible light.

6. The method, of claim 5, wherein the displaying comprises displaying a region, corresponding to a position of the photoacoustic material in the photoacoustic image, in a certain color.

7. The method of claim 5, wherein the displaying comprises displaying a shape of the light in a certain color, in the image expressing that the light is being irradiated onto the ROI.

8. The method of claim 1, wherein the displaying comprises displaying an image, in which the photoacoustic images respectively corresponding to the plurality of photoacoustic materials are combined, and an image in which images, expressing that light is being irradiated onto a plurality of ROIs respectively corresponding to the plurality of photoacoustic materials, are combined.

9. The method of claim 1, further comprising outputting a warning signal at a time when the light is irradiated onto the ROI of the object,
   wherein the warning signal is one of a signal corresponding to a certain sound, a signal corresponding to a certain text, a signal corresponding to a certain vibration, and a signal corresponding to a certain image.

10. A non-transitory computer-readable storage medium storing a program for executing the diagnostic image generating method of claim 1.

11. An apparatus for generating a diagnostic image, the apparatus comprising:
    a determiner configured to respectively determine a wavelength band of light maximally absorbed by a plurality of different photoacoustic materials, based on the plurality of different photoacoustic materials injected into an object;
    a light generator configured to generate lights corresponding to the respectively determined wavelength bands;
    an image generator configured to generate different photoacoustic images indicating an internal region of interest (ROT) of the object by using the different photoacoustic signals, wherein the different photoacoustic images correspond to the plurality of different photoacoustic materials respectively; and
    a display unit configured to combine the different photoacoustic images and the image expressing that the are being irradiated onto the RO and display the combined image.

12. The apparatus of claim 11, wherein the determined wavelength band of the light comprises a portion of a wavelength band corresponding to visible light.

13. The apparatus of claim 12, wherein the image generator configured to display a region, corresponding to a position of the photoacoustic material, in the photoacoustic image, in a color corresponding to the determined wavelength band.

14. The apparatus of claim 12, wherein the image generator configured to display a shape of the light in a color corresponding to the determined wavelength band, in the image expressing that the light is being irradiated on the ROI.

15. The apparatus of claim 11, wherein the determined wavelength band of the light comprises a portion of a wavelength band corresponding to light except visible light.

16. The apparatus of claim 15, wherein the image generator configured to display a region, corresponding to a position of the photoacoustic material in the photoacoustic image, in a certain color.

17. The apparatus of claim 15, wherein the image generator configured to display a shape of the light in a certain color, in the image expressing that the light is being irradiated onto the ROI.

18. The apparatus of claim 11, wherein the display unit configured to display an image, in which the photoacoustic images respectively corresponding to the plurality of photoacoustic materials are combined, and an image in which images, expressing that light is being irradiated onto a plurality of the ROIs respectively corresponding to the a plurality of photoacoustic materials, are combined.

19. The apparatus of claim 11, further comprising a warning signal output unit configured to output a warning signal at a time when the light is irradiated onto the ROI of the object, wherein the warning signal is one of a signal corresponding to a certain sound, a signal corresponding to a certain text, a signal corresponding to a certain vibration, and a signal corresponding to a certain image.

20. A system comprising:

a probe that irradiates different lights onto an internal region of interest (ROI) of an object to acquire a plurality of different photoacoustic signals corresponding to the irradiated lights; and a diagnostic image generating apparatus that generates the different lights which are to be irradiated onto the ROI, based on a plurality of different photoacoustic materials injected into the object, generates different photoacoustic images indicating the ROI and an image expressing that the different lights are being irradiated onto the ROI, by using the different photoacoustic signals, and combines and displays the generated different photoacoustic images.

* * * * *